United States Patent [19]

den Dunnen et al.

[11] Patent Number: 5,928,867
[45] Date of Patent: Jul. 27, 1999

[54] METHOD OF ISOLATING EXONIC GENE SEGMENTS OF EUKARYOTIC GENES, EXON TRAPPING VECTORS FOR USE THEREIN

[75] Inventors: Johan Theodorus den Dunnen, Rotterdam; Johanes Gregorius Dauwerse, Delft; Nicole Anne Datson, Leiden; Garrit Jan Boudewijn van Ommen, Amsterdam, all of Netherlands

[73] Assignee: Rijksuniversiteit Leiden, Leiden, Netherlands

[21] Appl. No.: 08/808,620

[22] Filed: Feb. 28, 1997

[51] Int. Cl.⁶ .............................. C12Q 1/68; C07H 21/02; C07H 21/04; C12N 15/00
[52] U.S. Cl. .......................... 435/6; 536/23.1; 536/24.3; 935/76; 935/77; 935/78
[58] Field of Search .............................. 435/6, 91.1, 91.2, 435/174, 172.1, 320.1, 240.2, 172.3; 536/23.1, 24.3, 24.33, 25.4, 25.41, 25.42

[56] References Cited

U.S. PATENT DOCUMENTS

| | | | |
|---|---|---|---|
| 5,252,475 | 10/1993 | Reth | 435/172.3 |
| 5,256,555 | 10/1993 | Milburn et al. | 435/195 |
| 5,492,817 | 2/1996 | Thompson | 435/68.1 |
| 5,559,019 | 9/1996 | Gui et al. | 435/240.1 |
| 5,627,064 | 5/1997 | Hoekstra | 435/194 |
| 5,665,563 | 9/1997 | Beckler | 435/68.1 |

FOREIGN PATENT DOCUMENTS

| | | |
|---|---|---|
| 742285 A1 | 11/1996 | European Pat. Off. . |
| WO9213071 | 8/1992 | WIPO . |

OTHER PUBLICATIONS

Lau et al., PNAS 80 : 5225–5229 (1983).
Jagadeeswaran et al., Gene 84 : 517–519 (1989).
The Stratagene Catalog, p. 39 (1988).
Datson et al., Nucleic Acids Research 24(6) : 1105–1111 (1996).
Auch et al., "Exon trap cloning: using PCR to rapidly detect and clone exons from genomic DNA fragments", *Nucleic Acids Research*, vol. 18, No. 22, pp. 6743–6744, Sep. 11, 1990.
Bione et al., "Identification of a novel X–linked gene responsible for Emery–Dreifuss muscular dystrophy", *Nature Genetics*, vol. 8, pp. 323–327, Dec. 1994.
Buckler et al., "Exon amplification: A strategy to isolate mammalian genes based on RNA splicing", *Proc. Natl. Acad. Sci. USA*, vol. 88 pp. 4005–4009, May 1991.
Chalfie et al., "Green Fluorescent Protein as a Marker for Gene Expression", *Science*, vol. 263, pp. 802–805, Feb. 11, 1994.
Cheng et al., "Effective amplification of long targets from cloned inserts and human genomic DNA", *Proc. Natl. Acad. Sci. USA*, vol. 91, pp. 5695–5699, Jun. 1994.

(List continued on next page.)

*Primary Examiner*—W. Gary Jones
*Assistant Examiner*—Ethan Whisenant
*Attorney, Agent, or Firm*—Trask, Britt & Rossa

[57] ABSTRACT

Method of isolating exonic gene segments of a eukaryotic gene by preparing a loaded exon trapping vector, bringing the loaded exon trapping vector in an environment in which transcription of DNA to RNA and RNA processing can occur, isolating processed RNA which includes exonic gene segments of the eukaryotic gene and, optionally, preparing a DNA copy of the isolated processed RNA. The loaded exon trapping vector comprises a large-insert DNA vector containing a segmented donor gene construct and, inserted in or close to said segmented donor gene construct, a target DNA fragment of at least 10 kb of eukaryotic genomic DNA. Use of vectors containing large genomic inserts allows to isolate exonic gene segments present in the correct transcriptional orientation as a complete set, without need for reordering individually isolated exons and verifying their continuity from isolated cDNAs. The number of false positives is much reduced, negatives (empty products) can easily be removed, and the system allows isolation of all types of exonic gene fragments, i.e. 5'-first internal and 3'-terminal exons.

11 Claims, 12 Drawing Sheets

OTHER PUBLICATIONS

Church et al., "Isolation of genes from complex sources of mammalian genomic DNA using exon amplification", *Nature Genetics,* vol. 6, pp. 98–105, Jan. 1994.

Colleaux et al., "Rapid physical mapping of YAC inserts by random integration of 1–Sce I sites", *Human Molecular Genetics,* vol. 2, No. 3, pp. 265–271, 1993.

Datson et al., "An Exon Trapping System Providing Size Selection of Spliced Clones and Facilitating Direct Cloning", *Identification of Transcribed Sequences,* pp. 169–181, 1994.

Datson et al., "Specific isolation of 3'–terminal exons of human genes by exon trapping", *Nucleic Acids Research,* vol. 22, No. 20, pp. 4148–4153, 1994.

Den Dunnen et al., "Reconstruction of the 2.4 Mb human DMD–gene by homologous YAC recombination", *Human Molecular Genetics,* vol. 1, No. 1, pp. 19–28, 1992.

Duyk et al., "Exon trapping: A genetic screen to identify candidate transcribed sequences in cloned mammalian genomic DNA", *Proc. Natl. Acad. Sci. USA,* vol. 87, pp. 8995–8999, Nov. 1990.

Hamaguchi et al., "Establishment of a highly sensitive and specific exon–trapping system", *Proc. Natl. Acad. Sci. USA,* vol. 89, pp. 9779–9783, Oct. 1992.

Heikoop et al., "Expression of the Human Dp 71 (Apo–Dystrophin–1) Gene from a 760–kb DMD–YAC Transferred to Mouse Cells", *Eur J Hum Genet,* pp. 168–179, 1995.

Huxley et al., "The Human HPRT Gene on a Yeast Artificial Chromosome is Functional When Tansferred to Mouse Cells by Cell Fusion", *Genomics* 9, pp. 742–750, 1991.

Ioannou et al., "A new bacteriophage P1–derived vector for the propagation of large human DNA fragments", *Nature Genetics,* vol. 6, pp. 84–89, Jan. 1994.

Krizman et al., "Efficient selection of 3'–terminal exons from vertebrate DNA", *Nucleic Acids Research,* vol. 21, No. 22, pp. 5198–5202, 1993.

Noteborn et al., "A Single Chicken Anemia Virus Protein Induces Apoptosis", *Journal of Virology,* vol. 68, pp. 346–351, Jan. 1994.

Pierce et al., "A positive selection vector for cloning high molecular weight DNA by the bacteriophage P1 system: Improved cloning efficacy", *Proc. Natl. Acad. Sci. USA,* vol. 89, pp. 2056–2060, Mar. 1992.

Podusio et al., "Detecting High–Resoluton Polymorphisms in Human Coding Loci by Combining PCR and Single–Strand Conformation Polymorphism (SSCP) Analysis", *Am. J. Hum. Genet.,* 49:106–111, 1991.

Roest et al., "Protein truncation test (PTT) for rapid detection of translation–terminating mutations", *Human Molecular Genetics,* vol. 2, No. 10, pp. 1719–1721, 1993.

Sarker et al., "Access to a Messenger RNA Sequence or Its Protein Product Is Not Limited by Tissue or Species Specificity", *Reports,* pp. 331–334, Apr. 21, 1989.

Selden et al., "Human Growth Hormone as a Reporter Gene in Regulation Studies Employing Transient Gene Expression", *Molecular and Cellular Biology,* vol. 6, pp. 3173–3179, Sep. 1986.

Tagle et al., "Magnetic bead capture of expressed sequences encoded within large genomic segments", *Nature,* vol. 361, pp. 751–753, Feb. 25, 1993.

Tinsley et al., "Apo–dystrophin–3: a 2.2kb transcript from the DMD locus encoding the dystrophin glycoprotein binding site", *Human Molecular Genetics,* vol. 2, No. 5, pp. 521–524, 1993.

Troutt et al., "Ligation–anchored PCR: A simple amplification technique with single–sided specificity", *Proc. Natl. Acad. Sci. USA,* vol. 89, pp. 9823–9825, Oct. 1992.

White et al., "Detecting Single Base Substitutions as Heteroduplex Polymorphisms", *Genomics* 12, pp. 301–306, 1992.

Zhuang et al., "Apoptin, a Protein Derived from Chicken Anemia Virus, Induces p53–independent Apoptosis in Human Osteosarcoma Cells", *Cancer Research* 55, pp. 486–489, Feb. 1, 1995.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO: 1:

AATAAA                                                                          6

(2) INFORMATION FOR SEQ ID NO: 2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO: 2:

TGTCTCCCTC CAGACCCCCA AGA                              23

(2) INFORMATION FOR SEQ ID NO: 3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO: 3:

ACGCTATGCT CCGCGCCCAT CGT                              23

(2) INFORMATION FOR SEQ ID NO: 4:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (xi) SEQUENCE DESCRIPTION: SEQ ID NO: 4:

```
CGGGATCCTA ATACGACTCA CTATAGGCGT CTGCACCAGC TGGCCTTTGA C          51
```

(2) INFORMATION FOR SEQ ID NO: 5:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 5:

```
CGGGATCCCG TCTAGAGGGT TCTGCAGGAA TGAATACTT                        39
```

(2) INFORMATION FOR SEQ ID NO: 6:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 6:

```
CGGGATCCTA ATACGACTCA CTATAGGACA GACCACCATG CAGCTGGCCT TTGACACCTA 60

CCAGGAG                                                          67
```

(2) INFORMATION FOR SEQ ID NO: 7:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 7:

```
CGGGATCCTA ATACGACTCA CTATAGGACA GACCACCATG GCAGCTGGCC TTTCACACCT 60

ACCAGGAG                                                         68
```

(2) INFORMATION FOR SEQ ID NO: 8:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO: 8:

```
CGGGATCCTA ATACGACTCA CTATAGGACA GACCACCATG GGCAGCTGGC CTTTGACACC 60

TACCAGGAG                                                        69
```

METHOD OF ISOLATING EXONIC GENE SEGMENTS OF EUKARYOTIC GENES, EXON TRAPPING VECTORS FOR USE THEREIN

FIELD OF THE INVENTION

The present invention relates to methods of genome analysis. Particularly, the present invention relates to the localization of genes associated with certain phenotypic traits and the identification of genetic defects associated with or causative of hereditary diseases. More particularly, the invention relates to a method of trapping segments of exons of eukaryotic genomic DNA. While the method of the invention is broadly applicable with respect to the genomic DNA of eukaryotic organisms, including genomic DNA from plants, insects, birds, yeasts and fungi, it is particularly applicable to methods of analyzing the genomic DNA of mammals (e.g., humans).

BACKGROUND OF THE INVENTION

To better understand the molecular basis of the phenotypic variability and hereditary disorders of a species, the first requirement is to identify the genes which are responsible for this variability. Current techniques to link specific phenotypes to specific chromosomal regions are very powerful, but the methods to identify genes within these regions are laborious and inefficient. Two basic methods to identify genes in cloned DNA can be distinguished, those dependent of the expression of the gene in question and those independent of it.

In the first mentioned type of gene identification methods, hybridization-based techniques are used to isolate RNA or cDNA which is homologous to the cloned genomic DNA of interest. Such techniques require adequate levels of expression, and thus knowledge of the tissue expressing the gene in question. The methods result in the isolation of any sequence hybridizing to the input DNA. Consequently, the identification of transcribed sequences is indirect and based on homology which may be incomplete, yielding related genes which in reality map elsewhere in the genome. Thus the obtained sequences have to be matched to the input sequence to prove their identity.

In the second type of methods, the cloned DNA is studied directly for its coding potential. The DNA can be sequenced and analyzed by computer for sequences predicting the presence of genes, e.g. CpG-islands, open reading frames, potential coding regions, splice donor and acceptor sites (delineating exons), promoter/5'-first exons, polyadenylation signal/3'-terminal exons, etc. However, the computer only calculates a likelihood and any 'gene' thus identified requires direct experimental proof. Alternatively, the region of interest can be cloned and tested for the presence of sequences which, given a suitable in vivo or in vitro splicing system, can be incorporated as exons in the processed mature RNA. This experimental protocol has been named 'exon trapping'.

Different variations of exon trapping have been described[1-8]. In general, cloned genomic fragments (e.g. total cosmid DNA) are subcloned in a special vector, between a splice donor (SD) and splice acceptor (SA) site. Individual subclones are picked, the DNA is isolated and introduced into a host cell (e.g. COS-cells). During propagation of the host cells, the introduced DNA is replicated and transcribed into RNA. After several days, total cellular RNA is isolated and vector-derived transcripts are amplified by RNA-PCR using vector-specific primers. Exons present in the cloned DNA will have been spliced between the known vector-derived exons and are thus 'trapped' in the RNA-PCR products. In a specific variation of exon trapping, designated 3'-exon trapping, the 3'-terminal exon of a gene is specifically isolated based on its ability to provide both a splice acceptor site and a polyadenylation signal[6,7].

At present, all these exon trapping variants suffer from major limitations, especially when complex sources of input DNA are used. In such cases, exon trapping becomes a laborious and insensitive technique which limits its use considerably. These limitations include:

a. The original clones, containing large segments of genomic DNA, need to be further subcloned in plasmid (or retroviral) vectors. To accommodate the insert capacity of these vectors, the inserts typically measure 2 kb or less. This step causes the genes to be fragmented into many separate and disconnected bits. Consequently, after trapping, individual exons rarely constitute a complete or even a substantially complete set of all the exons. Furthermore, any exons thus obtained have to be aligned to reconstruct their original order. This process is slow and inefficient and implies a major loss of information over the input material which contained the exons in the right order indeed.

b. Due to the small insert sizes after subcloning, most clones in the originally described systems do not contain any exons. Consequently, the RNA-PCR amplification step gives primarily small vector-to-vector products without an insert ('empty' products). These empty products are heavily enriched by the PCR-step, which favours the generation of small products. No efficient method has yet been presented to get rid of such products effectively without the disadvantage of the simultaneous removal of other, bona fide exons.

c. Many of the single exons which are trapped using any of the current methods are small (~120–150 bp) and often give poorly hybridizing probes for subsequent experiments, e.g. to screen cDNA-libraries. Furthermore, since the individually trapped exons require the use of cDNA-libaries in the next step to further define the gene, the initial advantage of working with an expression independent system is lost.

d. The vectors often contain internal, so called 'cryptic' splice sites resulting in a substantial proportion of false positives.

e. Subcloning disrupts the genomic context of the exons which results in a high background of false positives. Cloning of regions which are never transcribed or cloning of intronic sequences without their naturally flanking exons often results in activation of cryptic splice sites or spuriously coincident processing signals and thus leads to recognition of false exons.

f. The vectors can only be used in combination with specific cell lines (e.g. COS-cells), since they require a specific system of replication in the host cell, commonly based on the SV40 origin of replication.

Although 3' exon trapping is better in some respects, in that it traps larger exons and it identifies the end of a gene specifically, it does not provide a solution for the major limitations of the exon trapping technique in general.

SUMMARY OF THE INVENTION

The present invention uses the structure of eukaryotic genes (i.e. they are usually split into several pieces, the exonic gene segments of the exon) and the ability of transcripts to be initiated, elongated and terminated, as well as processed (i.e. spliced and polyadenylated) by the utilization of specific recognition sequences in the DNA supplied (FIG. 2). These signals are either used directly on the cloned genomic DNA of large-insert vectors (over 20 kb) or, after their transcription, from the resulting RNA.

The present invention provides a method of isolating, identifying, or isolating and identifying at least one gene segment of an exon of a eukaryotic gene, which includes functionally inserting an exon trapping DNA molecule comprising a gene segment of an exon into an exon trapping DNA molecule (i.e., "loading" the exon trapping molecule with the DNA molecule), introducing the loaded exon trapping DNA molecule into an environment in which transcription of DNA to RNA can occur, introducing the transcribed RNA into an environment in which processing can occur, and isolating or analyzing the processed RNA. Preferably, the loaded exon trapping vector comprises a known segment of an exon having known splice sites. An important aspect of the present invention is the transcription and splicing capability provided after loading the trapping vector, which enables the selection of coding regions. This transcription and/or splicing capability may be provided by a cell into which the trapping vector is introduced, but it may also be provided in an in vitro system. The latter is preferred. Thus, in a further embodiment, the invention provides a method as disclosed above whereby the loaded exon trapping DNA molecule is provided with at least one RNA polymerase promoter and whereby transcription occurs in an in vitro system in the presence of an RNA polymerase. It is, of course, preferred that the processing step is also carried out in vitro. Thus, in a further embodiment, the invention also provides a method whereby processing occurs in an in vitro system. It is, however, possible that splicing may occur in a host cell. Thus, in yet a further embodiment, the invention provides a method whereby the RNA transcript is injected into a eukaryotic host cell, allowing for processing of said RNA transcript. After either in vitro or in vivo transcription (optionally followed by splicing) the transcript may be subjected to amplification methods (e.g., PCR or nucleic acid sequence-based amplification (NASBA)) for direct identification or other purposes.

In a different embodiment applicable to all methods disclosed above, the exon trapping DNA molecule is a functional transposon. In this manner, the trapping molecule can be inserted in the genome of a host at any site and can be removed from the site. Together with the transcription and splicing capabilities provided this gives a very powerful exon trapping molecule, which is very useful in genome analyses. In a preferred embodiment, the transposase activity necessary for excision and/or insertion of the transposon trapping molecule is provided separated from the transposon trapping molecule, for instance on a separate vector, preferably under control of an inducible promoter so that transposase activity can be regulated in time and/or amount. Thus in a further embodiment the invention provides a method wherein said transposon does not encode functional transposase, but whereby the functional transposase is provided in trans.

In yet another embodiment the above is again carried out in a eukaryotic host cell, i.e. a method is provided wherein said environment in which transcription of DNA to RNA and RNA processing can occur, is a eukaryotic host cell, preferably a method wherein the eukaryotic host cell has a functional defect which can be complemented by a particular target eukaryotic gene. The applications of such a method are of course clear to a person skilled in the art. It gives a way of selection.

Another preferred method is one wherein the eukaryotic host cell is a representative of the cells or the tissue in which a particular target eukaryotic gene is naturally expressed, preferably a method wherein said eukaryotic host cell is a COS1 cell, a CHO cell, or a V79 cell. The invention is typically suitable for the isolation, identification and/or trapping of large target fragments, particularly preferred are methods wherein the target DNA fragment of eukaryotic genomic DNA is at least 20 kb. Preferably the target DNA fragment of eukaryotic genomic DNA is obtained directly from a eukaryotic cell, but it may also be obtained by subcloning from a library of cloned eukaryotic genomic DNA, such as from a cosmid or a YAC library.

The invention of course also provides an exon trapping DNA molecule comprising at least one functional promoter and at least one known exonic gene segment of an exon which is useful for carrying out the methods herein disclosed. Preferably such an exon trapping DNA molecule is a transposon for reasons given herein. Furthermore, the invention provides an exon trapping kit for carrying out a method according to the invention comprising an exon trapping DNA molecule as disclosed above. Preferably such a kit comprises an in vitro transcription system. In addition thereto, the kit preferably comprises an in vitro RNA processing system. A kit according to the invention may further comprise a set of oligonucleotide primers for amplification purposes, optionally together with enzymes and other means for carrying out amplification.

In yet another embodiment, the kit comprises at least one eukaryotic cell, transduceable with said exon trapping DNA molecule, whereby said kit preferably further comprises reagents for enabling said transduction. Amplification of the target DNA fragment may also occur in, for example, an *E. coli* strain.

According to our inventive method of isolating exonic gene segments and analysing them for the presence of mutations, large fragments of eukaryotic genomic DNA (i.e. over 20 kb) are inserted between, or 5' or 3' of segments of exons donated by a 'donor' gene on a large-insert vector (e.g., cosmid, P1, PAC, BAC or YAC). The clones are directly introduced, without further subcloning, into any eukaryotic host cell in which they are transcribed, resulting in the production and processing of RNA molecules. The vectors may have been engineered to contain additional sequences such that, when desired, translation of the RNA produces proteins which can be used to discriminate between individual constructs (e.g., to select out or kill cells containing exon-less inserts). The RNA of the cells is isolated and analysed. When exonic parts of a gene are present in the inserted DNA, they are paired with the exonic segments of the donor gene present in the vector construct and they produce fused gene products. These products can be isolated (e.g., by RNA-based PCR amplification) and the new, fused segments can be analyzed (FIGS. 3A & 3B). The products can be used to analyse the presence of open reading frames (e.g., by subsequent transcription and translation from suitable promoters and translation initiation sites contributed by tailed primers[9,10]) and, by comparing products derived from different genomic sources (e.g., a normal and a diseased individual), to directly detect genetic variations within them, including disease causing mutations.

In one preferred embodiment of the present invention, genomic fragments having compatible ends are cloned into the cosmid sCOGH1 at a BamHI-site created between exons 2 and 3 of the human growth hormone gene (hGH) which is driven by a mouse metallothionine-1 promoter (mMT1) (FIG. 4A). The resulting clones are transfected to COS1 cells by electroporation and high levels of transcription derived from the mMT1-promoter and/or a promoter cloned in the insert DNA. If the cloned region contains exonic gene segments of an exon, in the correct transcriptional orientation, processing of the RNA occurs in such a way that these gene segments become integrated into, or fused onto the exonic hGH-gene segments (FIGS. 3A & 3B) of the exon. For sCOGH1, culture medium can be used to perform a growth hormone assay; loss of hGH indicating that segments of a gene from the insert have disrupted the hGH-gene and thus precluded the production of the latter. Cytoplasmic RNA is isolated from the transfected cells and subjected to RNA-based PCR analysis using hGH-derived oligonucleotides. The amplified products contain the fused gene sequences and can be analysed, e.g. by cloning and sequencing, by direct sequencing or by translation.

According to alternative preferred embodiments of the present invention, not COS1-cells are used, but any other type of eukaryotic cells (e.g., V79, BHK) able to drive expression of the mMT1-promoter and able to produce correctly processed RNA. It may be advantageous to use other types of eukaryotic cells in order to secure a lower degree of homology between cloned and cell-derived sequences and the concomitant reduction of the background and subsequent simplified analysis of the products.

The method according to the above embodiments was used to isolate gene sequences from genomic clones in sCOGH1 containing known gene segments (i.e., parts of the human dystrophin gene). For each cloned 25–40 gene segment, the transfection resulted in the isolation of all known gene segments in one single RNA-PCR product. Subsequently, coupled transcription/translation was successfully used to detect the single known open reading frame out of the three possible reading frames.

The present method effectively copes with many of the limitations mentioned for the currently available methods of exon trapping. The vectors contain large genomic inserts and segments of exons present in the correct transcriptional orientation are isolated as a complete set, eliminating the need to reorder individually isolated exons and the need to verify their continuity from isolated cDNAs. Furthermore, since the genomic context in the clones remains intact, the number of false exons isolated is heavily reduced. The system is more flexible since it can isolate all types of fragments of exons; 5'-first, internal and 3'-terminal. The vectors used do not require a specific system for replication in the host cell and can be used in combination with any in vivo or in vitro system able to produce correctly processed RNA. In particular, due to the use of a strong ubiquitously expressed promoter, the necessity to use COS1-cells for RNA-processing is eliminated. This allows one to use other cell types (e.g. hamster V79 cells) in which the endogenous transcripts will have a lower degree of homology with the vector-derived gene. It also allows one to target specific segments of exons by testing directly whether the fused gene products obtained are able to functionally complement an existing defect in a specific cell type. Finally, the system facilitates an increased yield of RNA-products containing exonic inserts, including positive selection of transfected clones (e.g. neomycin selection for sCOGH1, FIG. 4A) and removal of transfected clones producing empty products (e.g., by induced cell death for sCOAP1, FIG. 4D).

The current invention facilitates several new strategies to identify genes and the presence of genetic variations in them. Isolation of genes expressed in specific tissues can be targeted e.g. by using a combination of a promoter/exon 1 less vector, a specific host system expressing the genes of interest and a 5'RACE protocol[29] on the isolated RNA. Identification of specific mutations in genomic DNA, especially mutations in splice sites and those disrupting the reading frame, can be realized e.g. by long distance PCR[11] on genomic DNA, incorporation of the product in sCOGH1, transformation of COS1-cells, RNA-isolation, RNA-PCR using tailed primers[9,10] and transcription and translation. This gives unique possibilities to identify mutations in the absence of knowledge of the entire structure of a gene, and without the availability of RNA from a patient, as well as for the analysis of one specific gene from a set of genes present in multiple expressed copies (e.g., the PKD1-gene) using gene-specific (e.g., intronic) primers.

BRIEF DESCRIPTION OF THE DRAWINGS

FIG. 3A shows that the 5'-RACE method targets 5'-first exons, including all co-cloned downstream exons. Internal PCR is used to isolate all cloned internal exons. The 3'-RACE method targets 3'-terminal exons, including all co-cloned upstream exons.

FIG. 3B shows, in clones in which the insert is cloned in the antisense orientation, no segments of exons are recognized and an 'empty' product results.

DETAILED DESCRIPTION OF THE INVENTION

Figure 1:
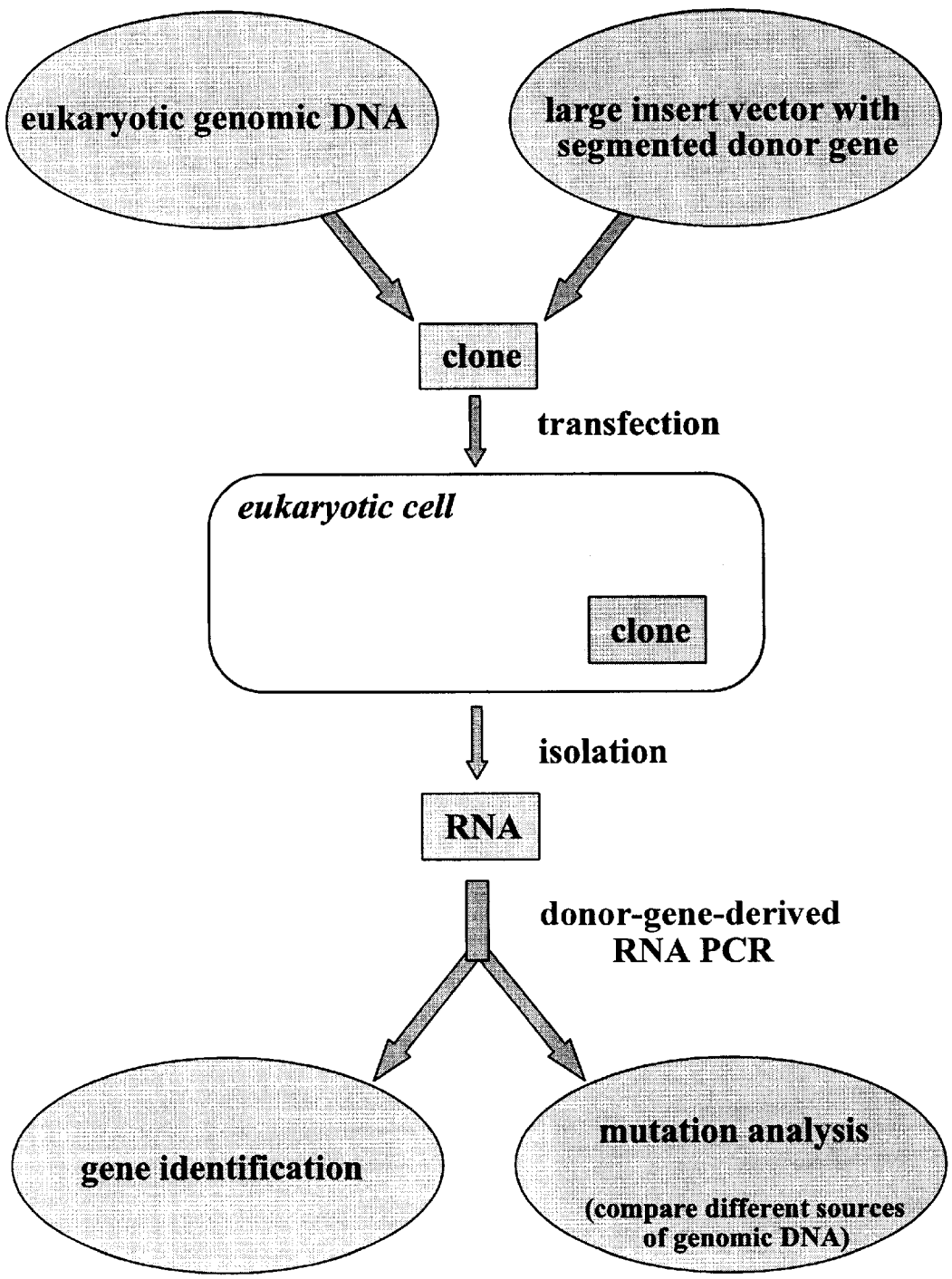
FIG. 1 gives a schematic representation of the invention.
Figure 2:
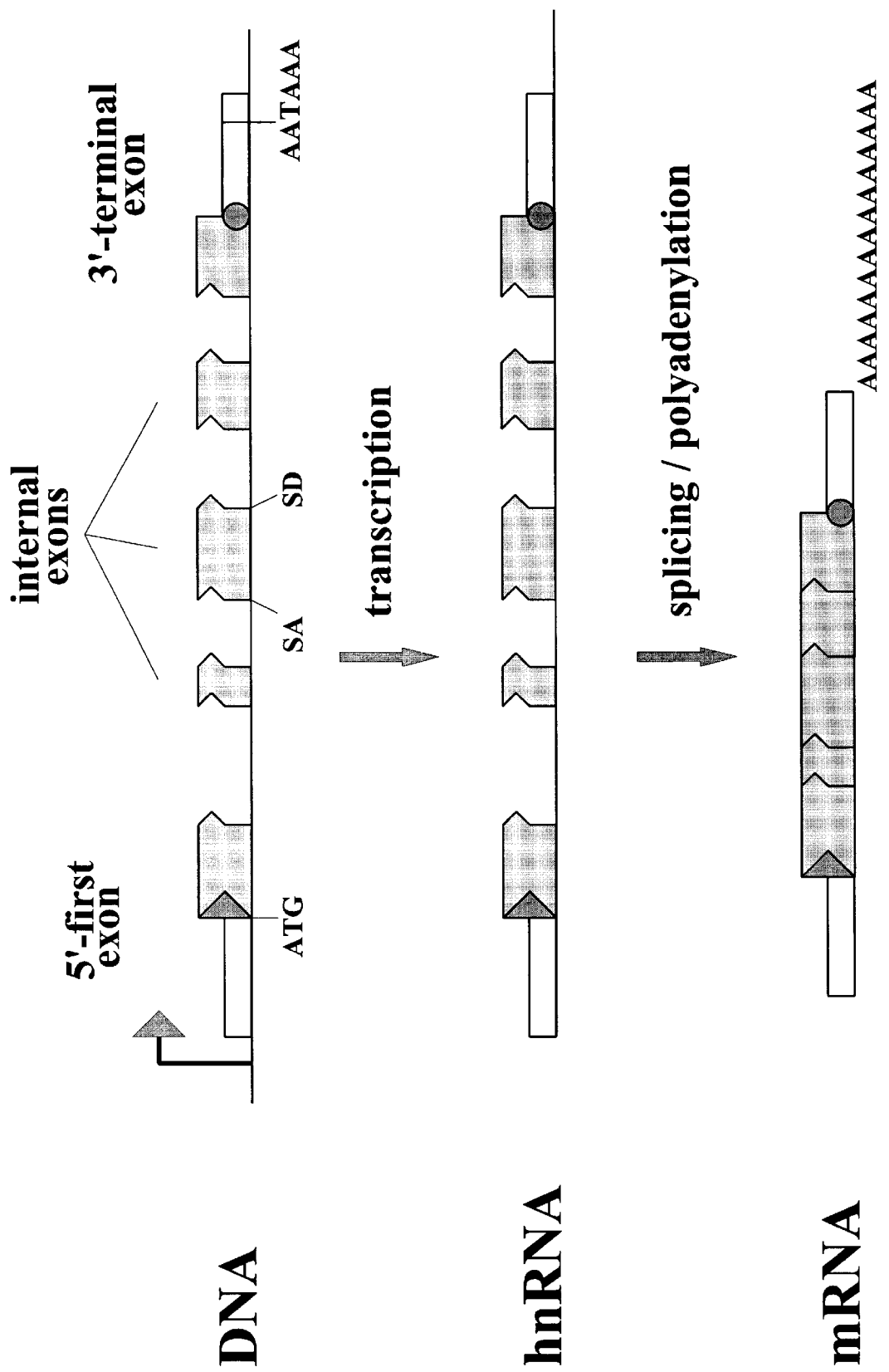
FIG. 2 gives a schematic picture of a segmented eukaryotic gene, and of transcription and RNA-processing. Segmented eukaryotic genes may contain up to 3 different types of exonic gene segments of exons; a 5'-first exon, no internal exons to over hundred internal exons, and a 3'-terminal exon, including a polyA-addition signal (here AATAAA (SEQ ID NO:1)). The primary RNA-transcript (hnRNA) is initiated from the promoter directly upstream of the 5'-first exon, elongates through the internal exons and terminates downstream of the 3'-terminal exon. Finally, hnRNA is processed i.e., splicing removes the intronic sequences and the RNA is polyadenylated just 3' of the polyA-addition signal, to yield the mature mRNA.
Figure 3A:
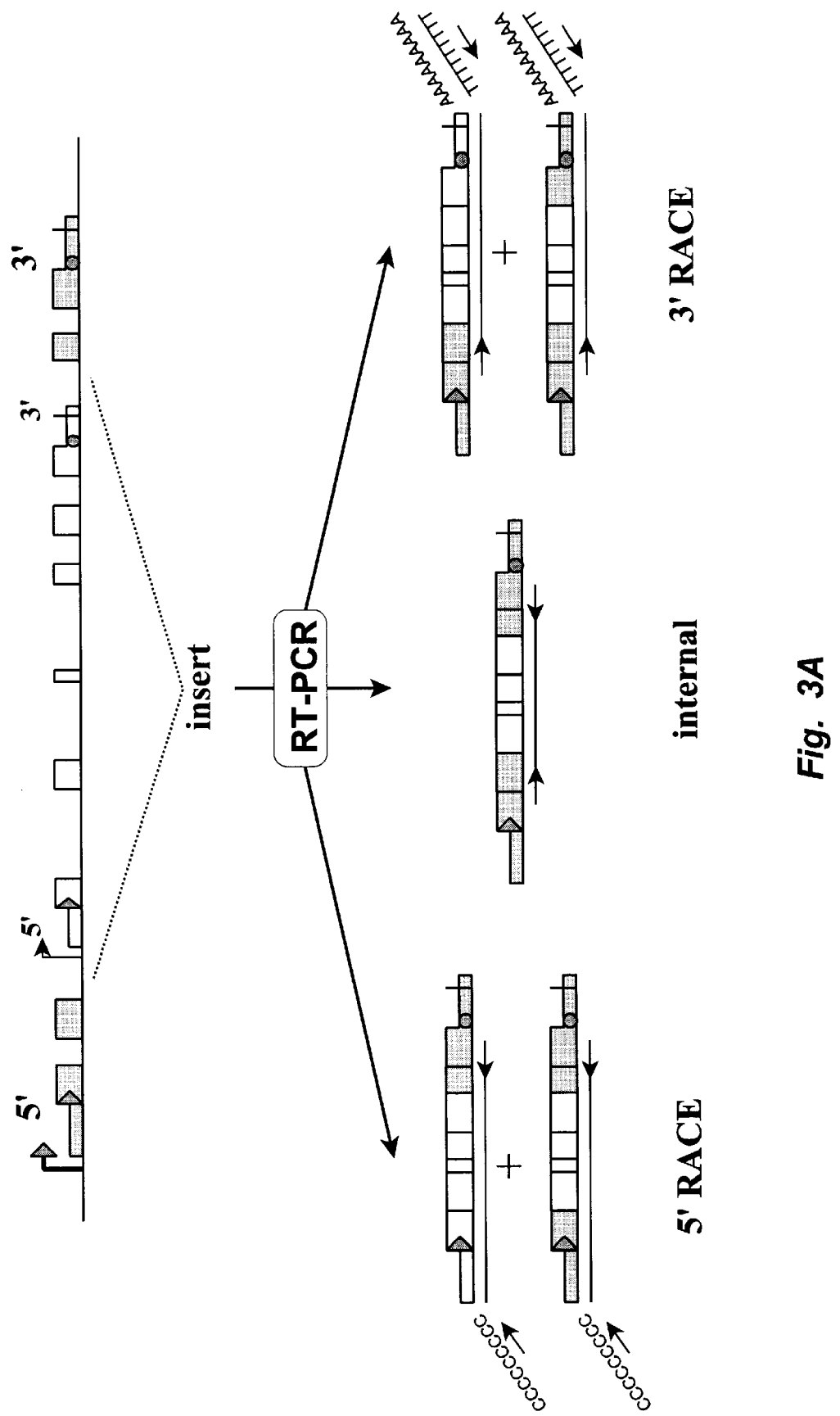
FIGS. 3A and 3B schematically illustrates the isolation of different segments of exons depending on the RNA-PCR method used. Depending on the type of segments of exons present and to be detected, 3 types of RNA-PCR are required.
Figure 3B:
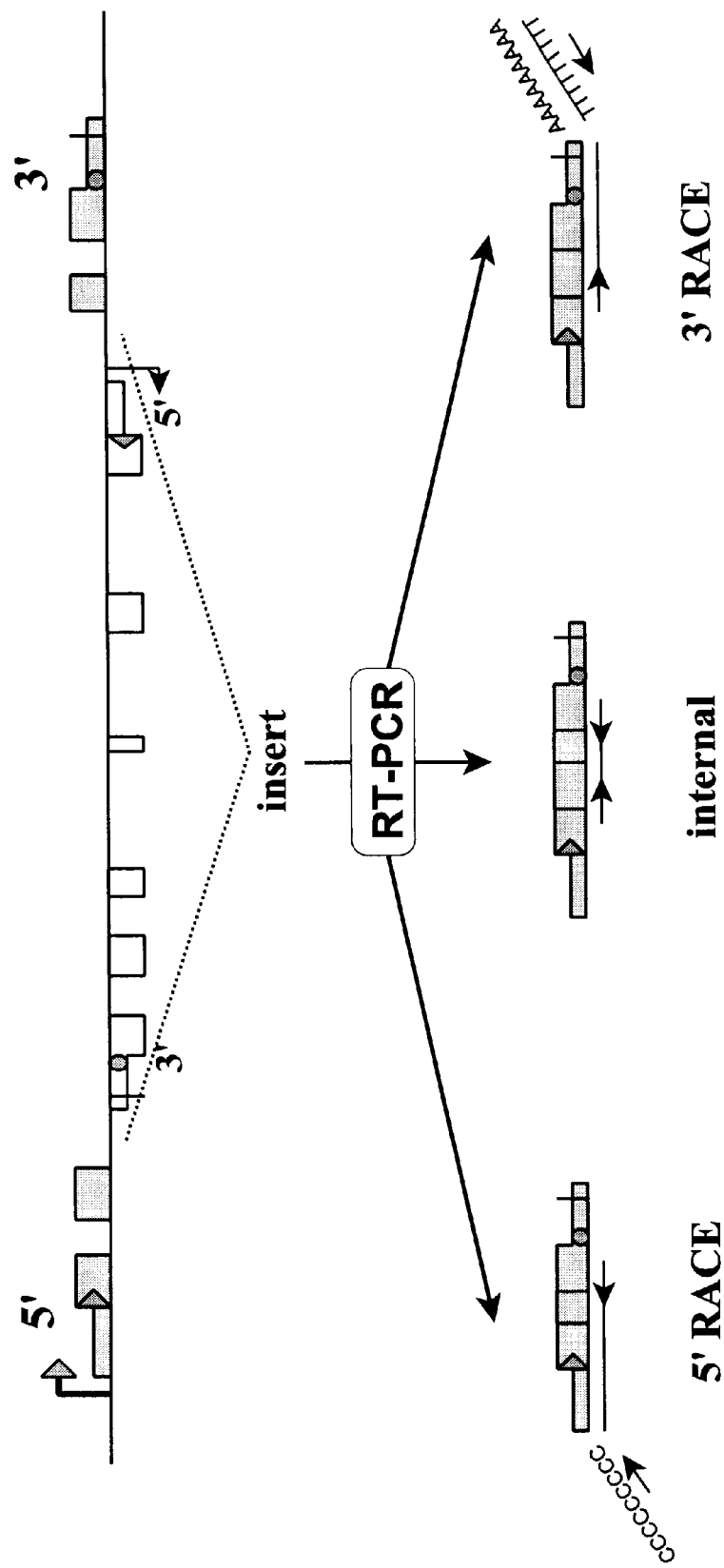

The present invention is a method of isolating exonic gene segments of exons based on the ability of transcription of DNA into RNA to be initiated, elongated and terminated as well as processed (i.e. spliced and polyadenylated) when the essential sequences for these processes are included in the DNA used. The method is useful for isolating gene sequences from genomic eukaryotic DNA and for the detection of sequence alterations (mutations) in these gene sequences.

Depending on their specific use, the vectors used with the present method contain sequences necessary for propagation in a host cell (e.g., a replication origin for E. coli or S. cerevisiae), selection in the host cell (e.g., resistance to antibiotics, such as ampicillin in E. coli or neomycin in mammalian cells, or required for growth, such as the HIS3- gene in *S. cerevisiae*), unique restriction enzyme site(s) (e.g., for cloning or linearization), targeting sequences homologous between vector and genomic DNA (e.g., the human Ala-repeat for fragmentation or insertion of YACs containing human inserts) and eukaryotic gene sequences serving as donor and/or acceptor of the gene segments to be detected by fusion to them (e.g., a strong promoter, such as the mMT1-promoter, or a gene, such as the hGH-gene) and/or enabling identification and removal of transfected clones which do not contain recognized and fused new segments of exons (e.g., LacZ, luciferase, GFP (green fluorescent protein[12]) and apoptin).

DNA to be introduced into the large-insert vectors may be directly taken from genomic DNA (e.g., from a cell, cloned genomic DNA such as a YAC or PCR-ed genomic DNA). Digestion with restriction enzyme(s) is used for the efficient insertion of the resulting fragments in the cloning site or sites in the vector. For example, in the case of sCOGH1, genomic DNA is partially digested with Sau3A to generate large fragments (i.e. 30–50 kb) which can be introduced into the BamHI-site of sCOGH1. In the embodiment of this procedure which is aimed at the direct study of genomic DNA in YACs, the procedure is inverted in that the vector elements are introduced into existing YACs, by homologous recombination in yeast cells holding these YACs, a procedure called 'retro-fitting'[3]. To increase the efficiency of this method, vector DNA to be introduced into the YACs can be digested with a restriction enzyme opening the DNA sequence homologous between vector and YAC DNA at which the in vivo yeast recombination is targeted.

The clones are propagated, DNA is isolated and introduced (e.g., by electroporation, lipofection or PEG-mediated cell fusion) into a host system able to produce initiated, elongated, terminated and processed RNA from this DNA (e.g., COS1 and V79 cells for mammalian DNA). RNA is isolated from these cells, using standard procedures[14], after propagation for two hours up to several days, with or without selection for the inclusion of the transfected DNA and/or against expression of the vector derived 'donor' gene only ('empty' clones).

Analysis of the isolated RNA can be performed in several ways (e.g., RNA-based PCR, Northern analysis and vector-primed cDNA-library construction) using standard protocols[14] and depending on the vector used, the type of segment (s) of exons of exons to be isolated and the results desired. RNA-based PCR starts with reverse transcription of the isolated RNA, primed with specific or random oligonucleotides. PCR can be performed in 3 different ways, targeting internal segments of exons, RNA transcription terminating gene segments (i.e., polyadenylation signal/3'-terminal exons) or RNA transcription initiating gene segments (i.e., promoter/5'-first exons). Internal gene segments derived from the inserted genomic DNA are isolated by using oligonucleotides flanking the insert DNA (e.g., a hGH exon 2 forward and hGH exon 3 reverse primer in the case of sCOGH1-clones). 3'-terminal exons, together with co-transcribed upstream exonic gene segments, are isolated by a 3'RACE reaction[6,7] (e.g., using a hGH exon 2 forward primer and a 5'-tailed oligo-dT prime[9,10] in the case of sCOGH1-clones). 5'-first exons, together with co-transcribed downstream segments of exons, are isolated by a 5'RACE reaction (e.g., after 5'-tailing of the RNA with RNA-ligase, by linker ligation to the reverse transcribed RNA[29], or by oligo-dT tailing of the reverse transcribed RNA using terminal deoxynucleotidyl transferase and subsequent PCR with a forward primer complementary to the added tail and a hGH exon 3 reverse primer).

Analysis of the RNA-derived PCR-products can be performed in several ways (e.g., cloning and sequencing, direct sequencing, to probe cDNA libraries, for transcription and translation, mutation analysis). One further embodiment of this invention allows direct analysis of the sample for the presence of open reading frames and occurrence of sequence variation (including mutations). For this, the hGH exon 2 forward primer is 5'-tailed with sequences, in this order, enabling T7-RNA polymerase transcription, eukaryotic translation initiation (i.e., a Kozak-sequence and ATG initiation codon) and either no, one or two additional nucleotides 5' of the hGH-sequence. Amplification of the RNA-derived PCR products using these three different tailed primers allow transcription by T7-RNA polymerase and translation of this RNA in an in vitro translation system (e.g., rabbit reticulocyte or wheat germ) with incorporation of labelled amino acids (e.g., $^3$H-Leu). Subsequent analysis of the three products (e.g., on SDS polyacrylamide gels) is used to determine if one of the products contains an open reading frame. Direct comparison of such products derived from different sources of input genomic DNA (e.g., a normal and a patient) allows the detection of variations in the sequences (mutations).

The large-insert vectors

Below, a few examples of large insert DNA vectors will be described which can be used to isolate segments of exons in the setting of this invention.

a. Cosmid vectors (FIGS. 4A–4D)

For propagation and selection in *E. coli* sCOGH1 (FIG. 4A) contains respectively, an *E. coli* replication origin (ori) and a gene conferring resistance to ampicillin (Amp). A unique XbaI-site allows linearisation of the vector and phosphatase treatment preventing self-ligation of the vector arms during cloning. The XbaI-site is flanked on both sites by two bacteriophage lambda-derived cos-sites (cos) which facilitate packaging and efficient introduction into *E. coli* after ligation of vector and insert DNA. The SV2neo-gene allows selection of cells transfected with the sCOGH1-clone using neomycin. The mouse metallothionine promoter 1 (mMT1) fused to the human growth hormone gene (hGH) contains a multiple cloning site (CS) with NotI and BamHI-sites facilitating cloning of genomic DNA fragments with compatible ends. The NotI-sites facilitate inversion of the insert by a simple digestion and religation protocol. Upon transfection of sCOGH1-clones into a suitable host system, the mMT1-promoter drives transcription of the hGH-gene and the inserted sequences. The ubiquitous and strong mMT1-promoter can be further induced by heavy metal ions (e.g., $Zn^{2+}$)[15] resulting in increased yields of vector-derived transcripts. The hGH-gene allows use of the culture medium for a growth hormone assay; the absence of hGH-activity indicating that segments of exons were present in the correct orientation in the inserted DNA, thereby precluding the production of hGH.

Specific variants of sCOGH1 can be constructed which target the isolation of 5'-first or 3'-terminal segments of exons specifically. sCOGH3 (FIG. 4B) differs from sCOGH1 by a deletion of the mMT1/hGH-exons 1 to 2 region (i.e. the promoter and 5' end of the gene). Due to the removal of the promoter and 5' end of the hGH-gene no RNA will be produced unless an insert contains an active promoter and a 5'-first segment of an exon. These 5'-exonic sequences can be isolated efficiently from the RNA by a 5'RACE protocol[29]. sCOGH5 (FIG. 4C) differs from sCOGH1 by deletion of the hGH-exons 3 to 5 (i.e. the 3' end of the gene). The removal of the 3' end of the hGH-gene results in the production of unstable mRNA unless an insert contains a 3'-terminal segment of an exon and a polyA-addition signal. The exonic 3'-gene segments can be isolated efficiently from the RNA by a 3'RACE protocol.

In other variants based on the structure of sCOGH1 the hGH-gene is replaced by other genes allowing identification, isolation, selection or specific killing of clones which do not produce RNA-PCR products with inserts but instead producing the normal gene product. For example, in vector sCOAP1 the hGH-gene present in sCOGH1 is exchanged for the avian apoptin gene[16,17] in which the PCR-amplified hGH intron 2 of sCOGH1 is introduced in the apoptin sequence at a unique restriction site in the coding region. When mixtures of sCOAP1-derived clones are transfected to an appropriate host system, their propagation will specifically kill those cells which were transfected by sCOAP1-clones producing empty products (i.e. no inserted exonic gene segments of exons) since these will produce apoptin which is lethal to the cell. This will considerably simplify the isolation of segments of exons, since it selects against the production of all 'empty' products (e.g., the 50% of clones which contain the insert in the wrong transcriptional orientation will be removed from the RNA-pool isolated).

Similar constructs can be envisaged in which the apoptin gene is exchanged with other genes allowing direct selection. Examples of this are, e.g., the thymidine kinase gene (TK), the LacZ-gene, the luciferase gene and the GFP-gene[12].

c. P1-vectors

The P1-based vectors, based on P1-vector pAD10SacBII[18] and the PAC-vector pCYPAC1[19], contain as an additional element the mMT1 promoter/hGH-gene element to facilitate the isolation and analysis of eukaryotic segments of exons. For example, PAC-vector pCYPAC-GH1 contains all the elements of pCYPAC1[19] with the following differences; the BamHI-pUC19-link is replaced by the mMT1/hGH element of sCOGH1 containing the BamHI-pUC19-link inserted in intron 2 of the hGH-gene.

d. YAC vectors

YACs (yeast artificial chromosomes) are linear DNA molecules which have a structure identical to the endogenous chromosomes of yeast, i.e., a left and right arm ending in telomeric sequences (TEL) and an additional sequence at the left arm functioning as a centromere (CEN). To study existing YAC-clones, constructs can be used which either insert into the existing clone (i.e., insertion vectors[13]) or which replace one of the two YAC-vector arms (i.e., fragmentation vectors[13]). For both vector types it is necessary to include a fragment in the vector which is identical to parts of the YAC (e.g., the YAC-vector arm, like the URA- or TRP-genes) or which has a high homology with sequences in the genomic insert of the YAC-clone (e.g., human repetitive DNA, like Alu- and LINE-sequences, for cloned human DNA). The combination of insertion vectors targeted at repetitive DNA sequences (e.g. Alu-repeats) is most fruitful. One retro-fitting experiment will yield a set of clones which contain an inserted copy of the integration plasmid at different sites throughout the YAC. Furthermore, since the orientation of the repetitive sequence in the insert differs from site to site, one experiment yields clones which allow scanning of the genomic DNA in both transcriptional directions for the presence of exonic gene segments. Upon recombination at the homologous sequences between vector and YAC-insert, YAC-fragmentation vectors exchange the YAC-arm, and all sequences up to the recombination site, for the vector-derived sequences. Since the targeted repetitive sequences are present throughout the YAC-insert, one fragmentation experiment yields a set of clones which fragmented the YAC-insert at different sites throughout the YAC, although all in the same transcriptional orientation. Consequently, to entirely scan a YAC-insert with fragmentation vectors it is necessary to use two constructs, one fragmenting the YAC from the right vector arm (R-arm) and one from the left vector arm (L-arm).

Vector pYAC-iGH1 is an insertion vector containing a replication origin (ori) allowing propagation in E. coli and one for replication in yeast (ARS), a marker for selection in E. coli (Amp, for resistance to ampicillin) and one for selection in yeast (HIS3), sequences (here cos-sites) facilitating shuttling to E. coli, the mMT1 promoter/hGH-gene element to isolate and analysis segments of exons, an Alu-repeat to target the construct to the human insert of a YAC-clone, unique sites facilitating analysis of the fragmented YAC-clones and allowing linearization of the vector construct to open the Alu-repeat, here AscI (necessary to increase the yield of recombinant clones) and an I-SceI site[20] to open the retrofitted YAC, enabling determination of the integration site.

Vector pYAC-fGH2 is a fragmentation vector replacing the right YAC vector arm. It contains a replication origin (ori) allowing propagation in E. coli and one for replication in yeast (ARS), a marker for selection in E. coli (Amp) and one for selection in yeast (HIS3), the mMT1 promoter/hGH-gene element to isolate the segments of exons, yeast telomere sequences to donate a new YAC-telomere after retro-fitting, an Alu-repeat to target the construct to the human insert of a YAC-clone, unique sites facilitating analysis of the fragmented YAC-clones and linearization of the vector construct in the Alu-repeat (here AscI) and sequences (here cos-sites) and a unique restriction site (here I-SceI) facilitating shuttling to E. coli.

Vector pYAC-fGH3 is a fragmentation vector replacing the centromeric left YAC vector arm. It is identical to pYAC-fGH2 but contains an additional segment with a yeast centromere sequence (CEN) to replace the left YAC-arm which is removed during recombination.

PCR-loaded exon trapping molecules.

In a specific variation of the system, the promoter/5'-first and 3'-terminal exon segments are provided by tailed primers enabling amplification of the target sequences. In these systems a 5'-tailed primer is used which adds an RNA polymerase promoter (e.g., T7 or T3) to the amplified sequence, enabling in vitro transcription of the PCR-fragment. The in vitro produced RNA can then be transferred directly into a system for RNA-processing (e.g., micro-injection into the nucleus of a eukaryotic cell, an in vitro splicing system, or a cell extract).

In another variation of the system, based on PCR-loaded exon trapping molecule, the 3'-terminal exonic gene segment is replaced by a primer which does not include a 3'-terminal segment of an exon but any sequence which would enable amplification of the target sequences (e.g., a primer annealing at repetitive DNA-sequences (e.g., Alu) or a random primer tailed with a known sequence facilitating subsequent specific PCR, or a primer adding a polyA-tail to the amplified target sequence). Analysis of such loaded exon trapping molecules after transcription in RNA-processing is performed using the known 5'-sequences and the added 3'-sequences.

In another variation based on PCR-loaded exon trapping molecule, the 5'-first segment of an exon is replaced by a primer which does not include a 5'-first exon segment but any sequence which includes an RNA polymerase promoter (e.g., T7 or T3) and which enables amplification of the target sequences (e.g., a primer annealing at repetitive DNA-sequences (e.g., Alu) or a random primer tailed with a known sequence facilitating subsequent transfer to a system for RNA-processing (e.g., micro-injection into the nucleus of a eukaryotic cell, an in vitro splicing system, or a cell extract).

In another variation based on PCR-loaded exon trapping molecule, the 5'-first segment of an exon is replaced by a primer which does not include a 5'-first exonic gene segment nor an RNA polymerase promoter sequence. Due to the removal of the promoter and 5'-first segment of an exon, no RNA will be produced after transfer to the transcription system unless the loaded segment of an exon contains an active promoter and a 5'-first segment of an exon. These 5'-exonic sequences can be isolated efficiently from the processed RNA by e.g. a 5'RACE protocol.

EXAMPLES

I Isolation and cloning of exonic dystrophin gene segments from YAC-derived human genomic DNA using a cosmid vector To demonstrate the ability of the present method to isolate segments pf expms from eukaryotic mammalian DNA, we subcloned a YAC known to contain the human dystrophin gene[21] in sCOGH1. Herein follows a description of the materials and methods used to identify the exonic gene fragments of exons in the sCOGH1-clones obtained.

Figure 4A:
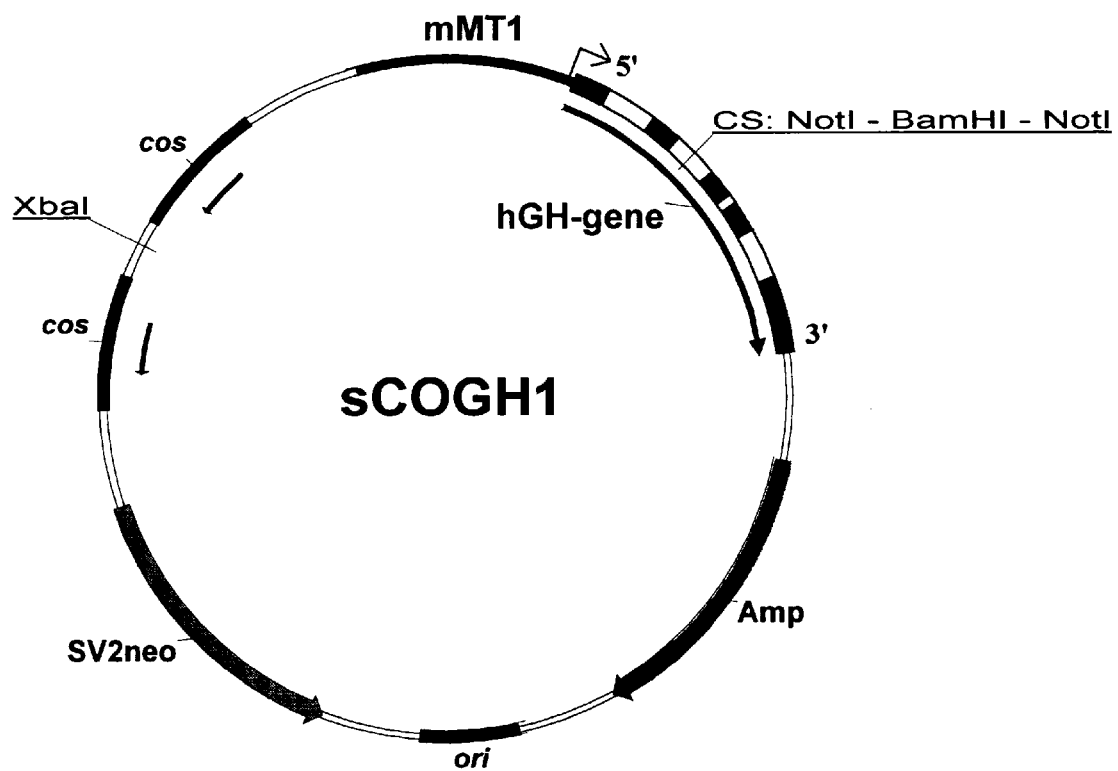
FIGS. 4A through 4H gives examples of large insert vector constructs. Cosmid vectors sCOGH1 (FIG. 4A), sCOGH3 (FIG. 4B), sCOGH5 (FIG. 4C) and sCOAP1 (FIG. 4D). PAC vector pCYPAC-GH1 (FIG. 4E). YAC integration vector pYAC-iGH1 (FIG. 4F) and YAC fragmentation vectors pYAC-fGH2 (FIG. 4G) and pYAC-fGH3 (FIG. 4H).
Figure 4B:
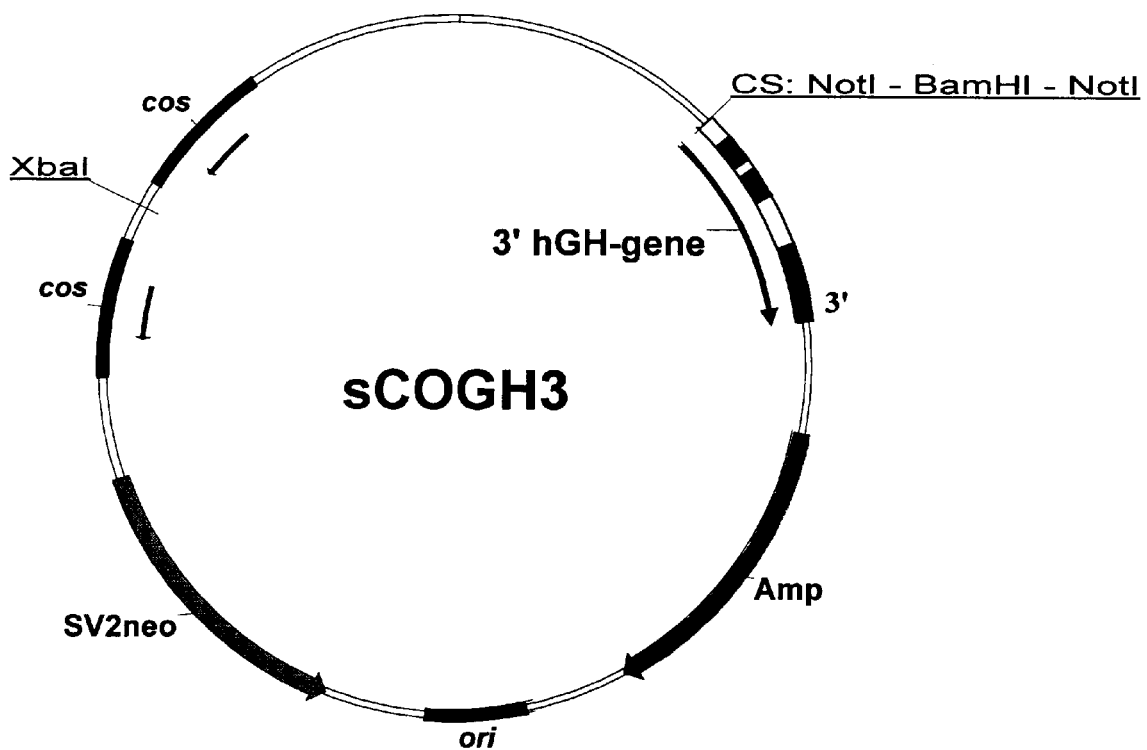
Figure 4C:
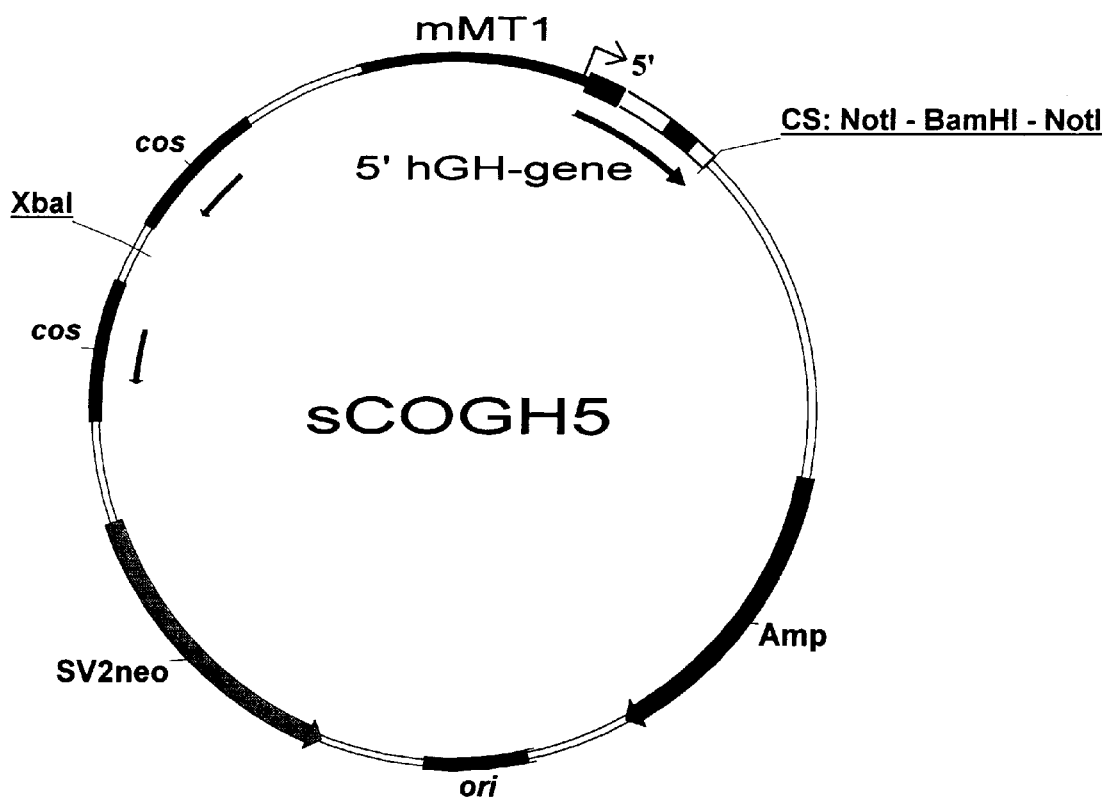
Figure 4D:
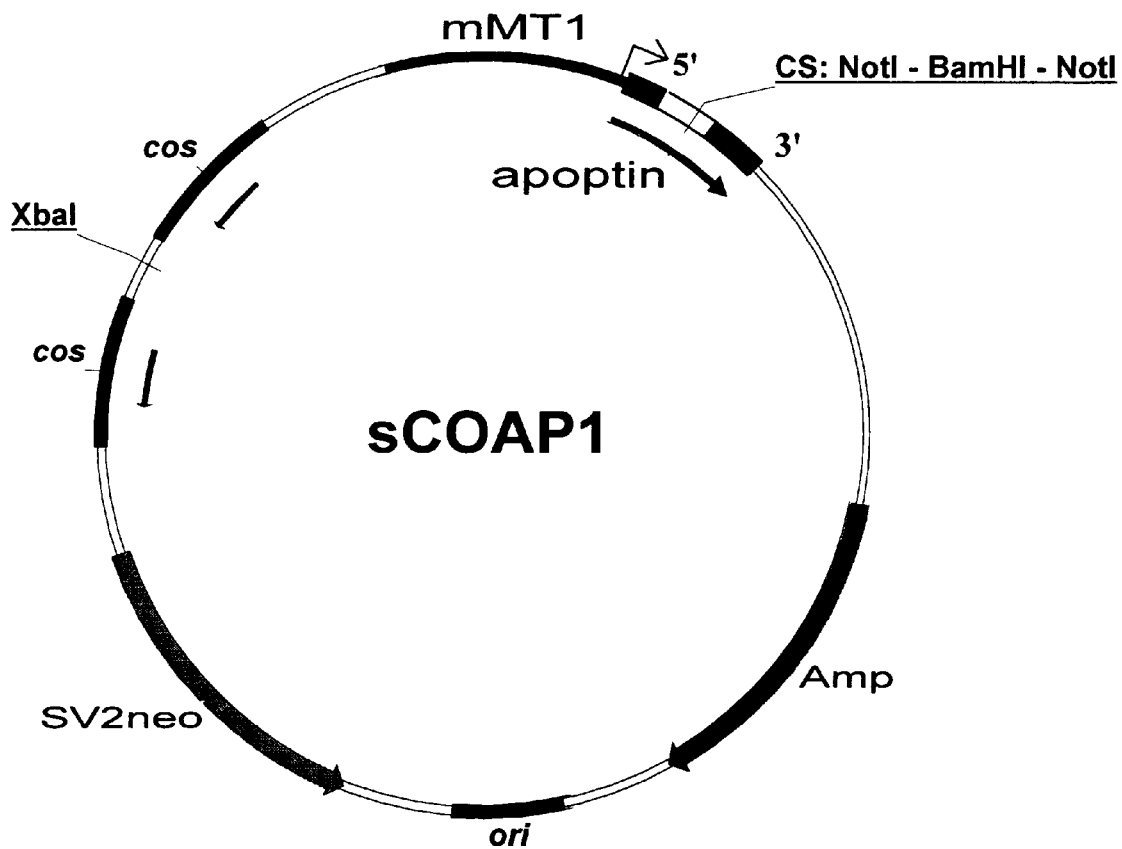
Figure 4E:
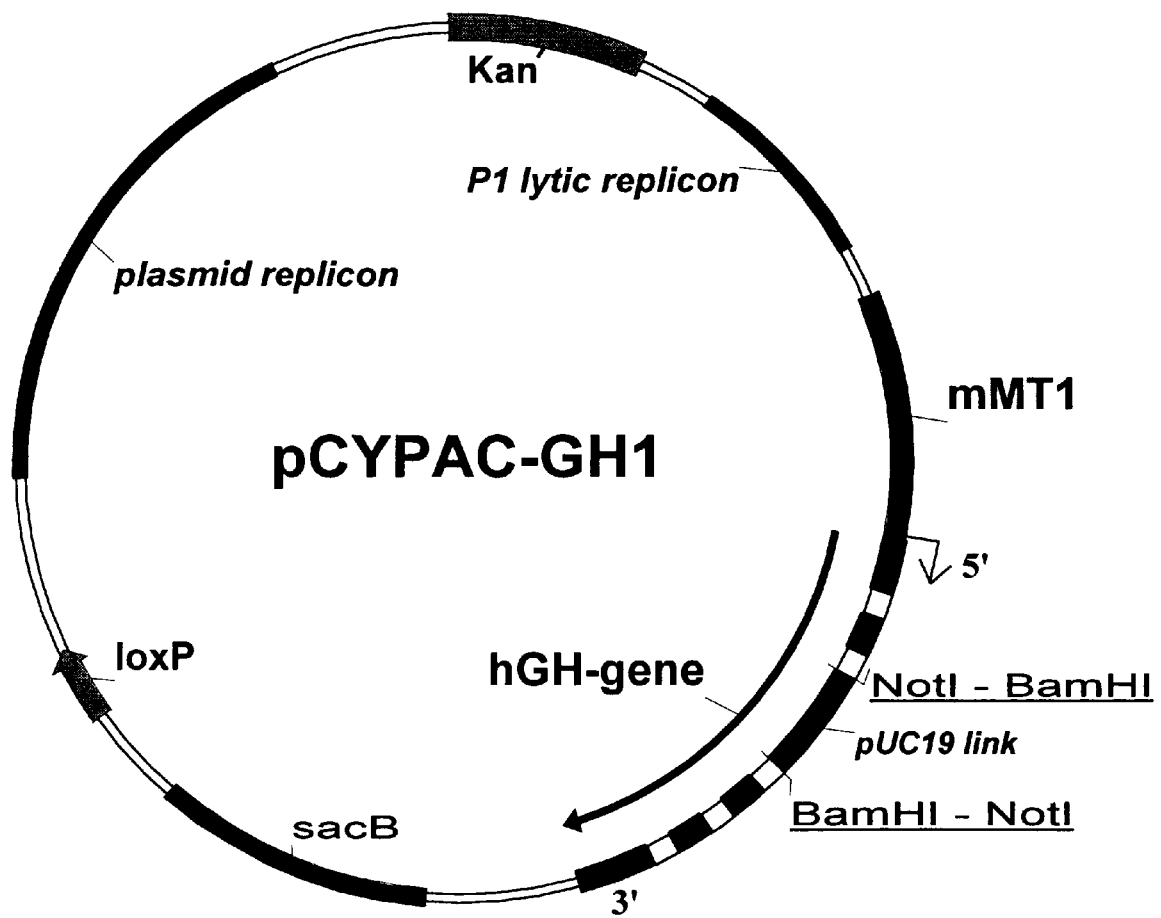

Vector sCOGH1 sCOGH1 is drawn schematically in FIG. 4A. sCOGH1 was constructed as follows: cosmid vector sCOS1 was digested with EcoRI and the vector DNA was purified by agarose gel electrophoresis and elution. Similarly, plasmid pXGH5[15] was digested by EcoRI and the fragment containing the mMT1/hGH-gene was isolated by gel-purification. Both fragments were combined by ligation, resulting in the isolation of sCOGH0a and sCOGH0b, differing in the orientation of the mMT1/hGH-insert in the sCOS1. A cloning site was introduced in intron 2 of the hGH gene by digestion of sCOGH0b with AccI and ligation with a linker containing NotI and BamHI sites.

Construction of cosmid libraries in sCOGH1

Vector sCOGH1 was propagated in *E. coli* strain 1046. For cosmid cloning, sCOGH1 DNA was prepared by linearisation with XbaI, dephosphorylation and subsequent digestion with BamHI. Agarose plugs containing total yeast genomic and YAC DNA of yDMD(0–25)C, containing the human DMD-gene from 100 kb upstream of the brainexon 1 to 100 kb downstream of exon 79[21], were partially digested with MboI, size fractionated and ligated into the BamHI-site of sCOGH1. The ligated material was packaged using GIGAPACK™ Plus Packaging Extract (Stratagene) and used to transform *E. coli* 1046. Clones containing specific regions of the dystrophin gene were isolated and analysed using standard protocols[14] by hybridization with specific dystrophin cDNA sequences[21].

Cell culture and electroporation

COS1-and V79 cells were cultured in DMEM with 10% inactivated fetal calf serum (GIBCO BRL). Cosmid DNA was introduced by electroporation. Cells were collected by centrifugation, washed in cold PBS (without bivalent cations), resuspended in cold PBS at a density of $2 \times 10^7$ cells/ml. 0.5 ml of cell suspension was added to 20 ml of PBS containing 10 mg cesium-chloride purified cosmid DNA and placed in a prechilled electroporation cuvette (0.4 cm chamber, BioRad). After 5 minutes on ice the cells were electroporated in a Biorad GENE PULSER™ (300 V [750 V/cm]; 960 mF) and placed on ice again. After 5 min the cells were transferred gently to a 100 mm tissue culture dish containing 10 ml of prewarmed, equilibrated DMEM+10% FCS. Transfection efficiency was tested in 100 ml of the culture medium of cells transfected with pXGH5 by assaying the hGH-concentration using the ALLEGRO™ hGH Transient Gene Assay Kit (Nichols Institute, San Juan Capistrano, USA).

RNA isolation, RNA-PCR and product analysis

48–72 hours after transfection the cells were harvested and total RNA was isolated using RNazolB (CINNA/BIOTECX). First-strand cDNA synthesis was performed by adding 100 pmol of primer hGHf (3'-TGTCTCCCTCCA-GACCCCCAAGA-5'(SEQ ID NO:2)) to 5 mg total RNA in a volume of 32 ml. The mixture was incubated at 65° C. for 10 min and chilled on ice. 28 ml of a mix containing 6 ml 0.1 M DTT, 6 ml 10 mM dNTPs, 1 ml RNasin (40 units/ml) (Promega), 12 ml 5×RT buffer (250 mM Tris-HCl pH 8.3, 375 mM KCl, 15 mM $MgCl_2$; GIBCO BRL) and 600 units SUPERSCRIPT™ Reverse Transcriptase (GIBCO BRL) were added to a final volume of 60 ml, and incubated at 42° C. for 1 hour. Subsequently, the solution was heated to 95° C. for 5 min and chilled on ice. 4.5 units of RNase H (Promega) were added and the solution was incubated at 37° C. for 20 min. 10 ml of the solution was used in a PCR reaction containing 12.5 pmol of primer hGHe (5'-ACGCTATGCTCCGCGCCCATCGT-3'(SEQ ID NO:3)), 50 mM KCl, 1.5 mM $MgCl_2$, 10 mM Tris.HCl pH 8.0, 0.2 mM dNTPs, 0.2 mg/ml BSA and 0.25 units SUPERTAQ™ (HT Biotechnology Ltd) in a reaction volume of 50 ml, followed by an initial denaturation step of 5 min at 94° C., 35 cycles of amplification (1 min at 94° C., 1 min at 60° C. and 3 min at 72° C.) and a final extension of 10' at 72° C. No additional hGHf primer was added in the PCR reaction. Nested PCR, using either internal hGH-primers or combinations of a hGH-primer and a DMD-primer, was performed on 1 ml of the primary PCR material with 12.5 pmol of each primer and PCR conditions identical to the first PCR. The internal hGH-primers used were hGHa (5'-CGGGATCCTAATACGACTCACTATAGGCGT CTGCACCAGCTGGCCTTTGAC3'(SEQ ID NO:4)) and hGHb (5'-CGGGATCCCGTCTAGAGGGTTCTGCA-GGAATGAATACTT-3'(SEQ ID NO:5). When RNA-PCR products were used for in vitro transcription and translation, primer hGHa was replaced by hGHaORF1f (5'-CGGG-ATCCTAATACGACTCACTATAGGACAGACCACC ATGCAGCTGGCCTTTGACACCTACCAGGAG-3'(SEQ ID NO:6)), hGHaORF2 (5'-CGGGATCCTAATACGACT-CACTATAGGACAGACCACCATGGCAGCTGGCCTTF-CACACCTACCAGGAG-3'(SEQ ID NO:7)) or hGHaORF3 (5'-CGGGATCCTAATACGACTCACTATAGGACA-GACCACCATGGGCAGCTGGCCTTGACACCTACCA-GGAG-3'(SEQ ID NO:8)). Direct sequencing of PCR products was carried out using the SEQUENASE™ PCR Product Sequencing Kit (USB).

Results

Clones cDMD2f, cDMD3f and cDMD17f were isolated containing, respectively, exons 72–76, exons 68–74 and exon 45, in the correct transcriptional orientation. All clones were digested with NotI, religated and packaged to obtain clones with the antisense orientation, designated cDMD2r, cDMD3r and cDMD17r, respectively. Each clone was introduced individually into COS1 and/or V79 cells and RNA was isolated as described.

To demonstrate that the system can be used in different eukaryotic cell lines, we transfected the clones cDMD2f and cDMD3f to both COS1 cells (monkey) and V79 cells (hamster). RNA-PCR analysis showed that both cell lines produced the expected full-size products (see below). However, V79 cells gave significantly higher yields and were used in further experiments. The successful use of other than COS1 cells can be used to reduce the background of products derived from the cell type used. Other strong promoters, such as PGK, have the same effect and can further assist in adapting these methods to many other host cell systems.

In all cases, RNA-PCR analysis of the RNA isolated from the transfected cells yielded products containing the exonic DMD-segments. The exonic content of the products was deduced by sequencing and/or hybridization to genomic DNA. In the case of cDMD2f, RNA-PCR analysis produced a product of 0.79 kb containing the DMD exons 68–74. All exons were spliced correctly onto each other and DMD exon 68 to hGH-exon 2. DMD exon 74 was not spliced to hGH-exon 3. Sequence analysis showed that the exon 74 splice donor site was incomplete, the insert of cDMD2f ended exactly in this site. cDMD2r, containing the exonic DMD segments in the antisense orientation, gave the empty hGH exon 2/exon 3 product but no insert-derived products. RNA-PCR analysis of cDMD3f yielded a product of 0.83 kb containing DMD exons 72–76. All exons were spliced correctly onto each other, DMD exon 72 to hGH-exon 2 and DMD exon 76 to hGH-exon 3. cDMD2r produced no insert-derived products. RNA-PCR analysis of cDMD17f gave a 0.28 kb product containing DMD exon 45 spliced in between of hGH-exons 2 and 3. cDMD17r yielded a 0.35 kb product, the origin of which was not yet determined.

Next to the 0.83 kb cDMD2f product described, the RNA-PCR analysis yielded an extra product of 0.79 kb. Sequence analysis showed that this product was identical to the 0.83 kb product except for the absence of exon 71. Since in normal human tissues exon 71 is also differentially spliced, this finding shows that the sCOGH1-system is capable of faithful transcription and processing of the segments of exons in the cloned DNA-inserts.

A 3'RACE analysis of clones cDMD2f and cDMD3f was performed to determine the capability of the method to isolate 3'-terminal segments of exons. cDMD2f produced a 0.8 kb fully spliced product containing hGH-exon 2/DMD-exons 72–76/hGH-exons 3–5. cDMD3f, however, produced a 0.85 kb fragment containing hGH-exon 2 and DMD-exons 68–70 ending in a polyadenylated sequence derived from intron 70. The exon70/intron 70 sequence is known to be used as an alternative 3'-terminal segment of an exon[22]. Consequently, the experiment demonstrates the capability of the method to isolate 3'-terminal segments of exons.

II Scanning complex, uncharacterized genomic regions for the presence of exonic gene segments To scan large genomic regions for the presence of segments of exons the region of interest (e.g., a YAC covering a disease gene candidate region) is first cloned in one of the large-insert vectors (e.g., sCOGH1). Cosmid clones containing inserts of the YAC are isolated, mixed, used to transfect V79 cells and the isolated RNA is analysed by RNA-PCR for products larger than the products obtained by sCOGH1 only. In this situation the predominant RNA will contain the 'empty' vector sequences only, since in 50% of the clones the insert has the antisense orientation. Removal of these sequences can be achieved in several ways, e.g., by a size selection of the initial RNA-PCR products obtained or by solution hybridization of a biotinylated oligonucleotide, which covers the hGH exon 2/exon 3 junction, to the DNA-strand synthesized by reverse transcription and removal of the hybrid molecule with magnetic beads[23].

Alternatively, vectors like sCOAP1 can be used, which prevent the production of empty products (see above). Depending on the complexity of the RNA-PCR products obtained, individual fragments are, e.g., excised from a gel and analysed directly (e.g., by translation to detect large open reading frames) or the mixture of products is cloned and individual cloned inserts are analysed.

Figure 4F:
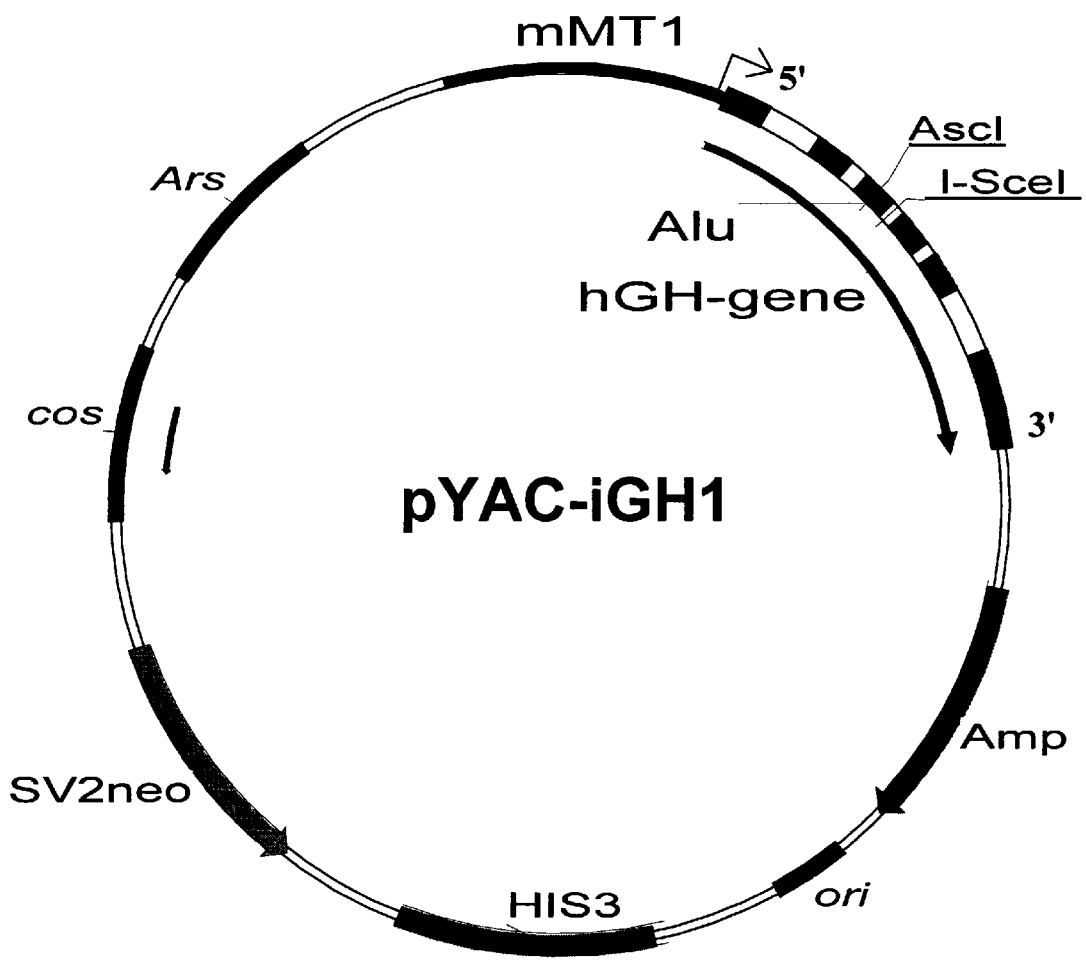
Figure 4G:
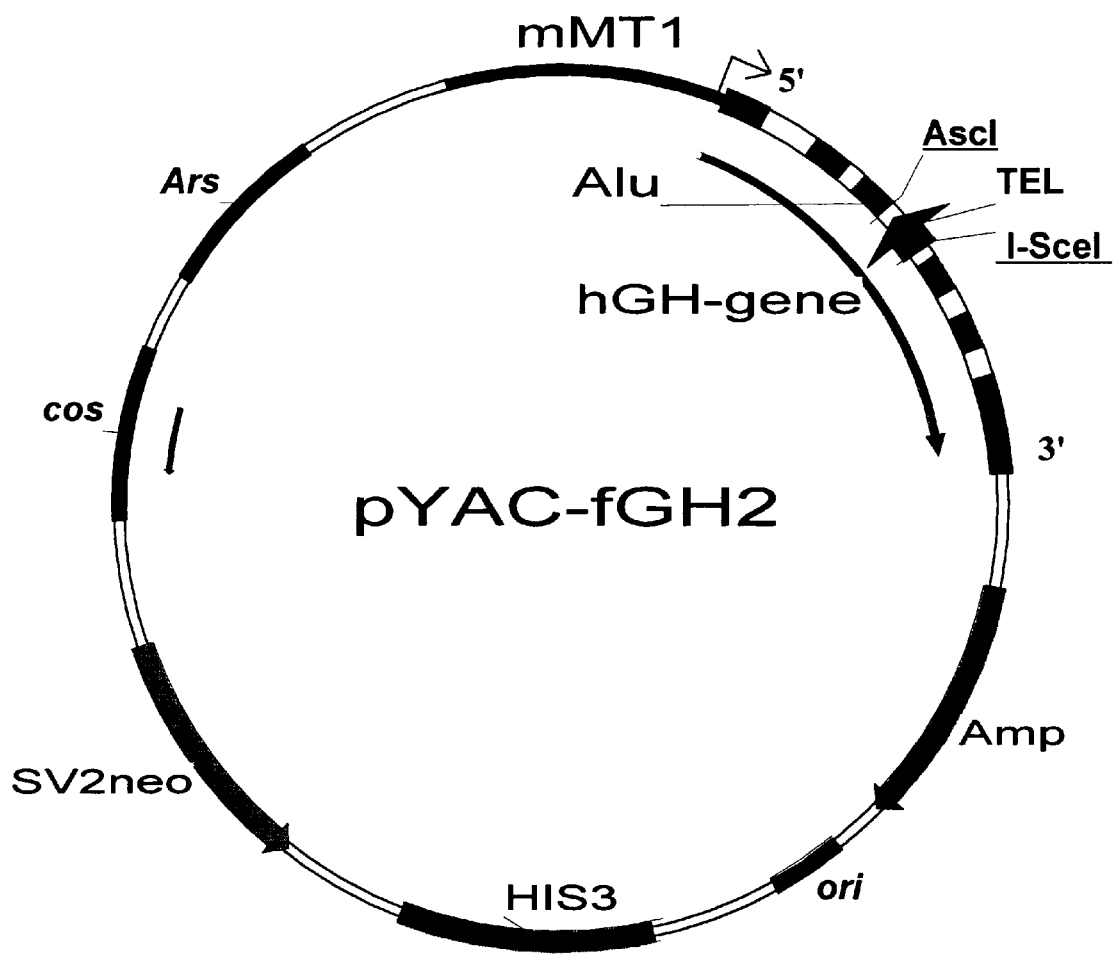
Figure 4H:
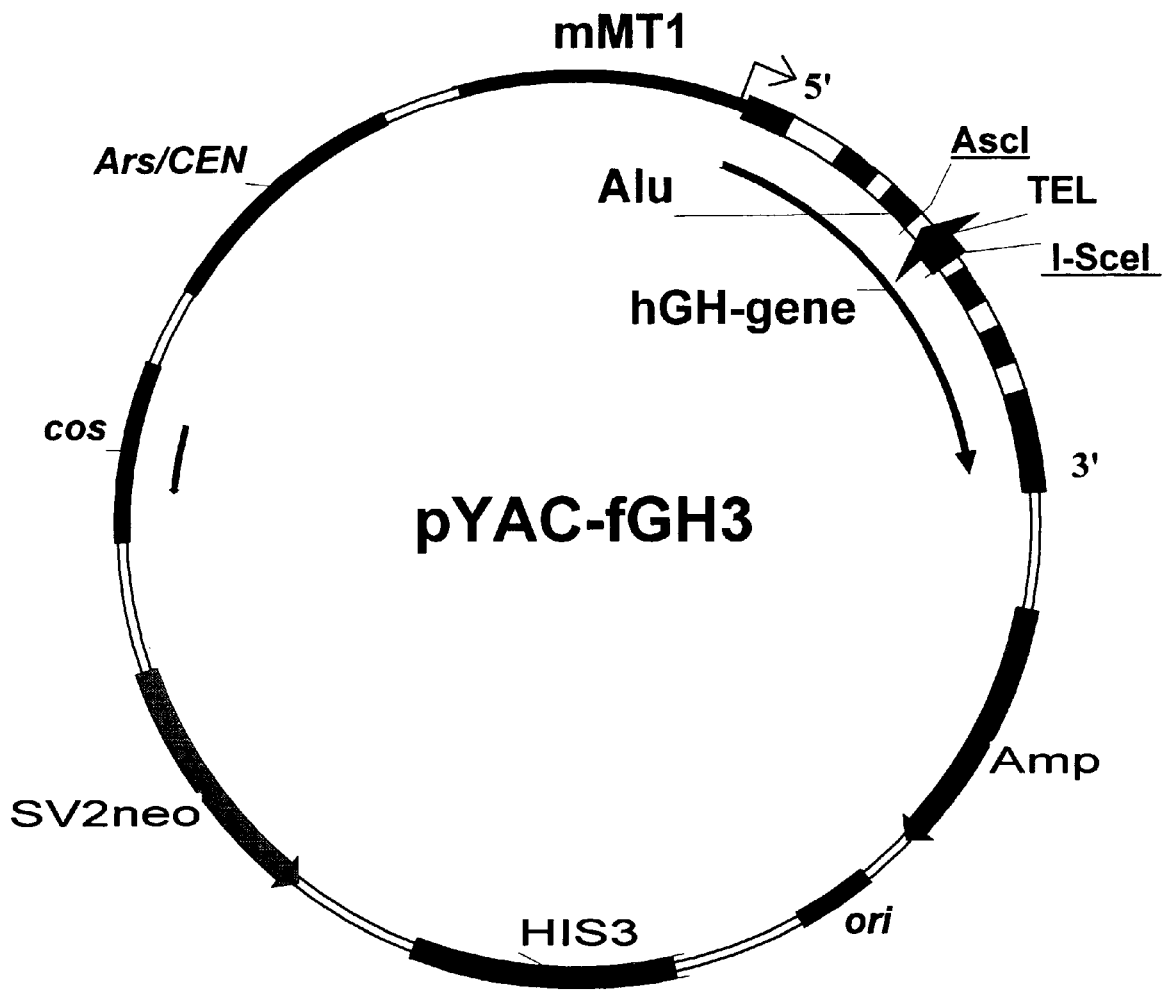

III Scanning YACs for exonic gene segments using integration and/or fragmentation vectors Fragmentation and retrofitting with insertion vectors of individual YAC-clones is performed according to standard protocols[13] using the linearized vectors described (e.g., pYAC-iGH1 FIG. 4F). Individual retrofitted YAC-clones can be used to transfect eukaryotic cells (e.g., V79 cells) using published protocols[24,25] and RNA is isolated after several days of propagation (with or without selection for transfected cells and/or against cells producing empty products). Analysis of the RNA isolated from the transfected cells is performed as described above (Examples I and II).

Since transfection of eukaryotic cells with YACs is usually inefficient, the integration and fragmentation vectors contain sequences and restriction sites which facilitate shuttling of large pieces of the YAC insert to E. coli, thereby giving easier access to sufficient DNA and thus successful transfections. pYAC-iGH1, for example, contains a unique I-SceI site, just downstream of the cloning site in intron 2 of the hGH-gene, which releases the inserted DNA from one end of the vector. In combination with digestion by another restriction endonuclease, which does not cut in the vector, this releases the other end of the YAC-insert. Subsequent addition of a suitable adaptor, able to join both ends, allows formation of circular molecules by ligation. These molecules can be used to transfect E. coli since they contain all elements essential for their selection and propagation.

IV Isolation of tissue specific 5'-gene segments from human genomic DNA using a cosmid vector The current invention facilitates the targeted isolation of genes expressed in specific tissues. This possibility can be used in positional cloning efforts directed at the isolation of genes involved in the development of genetic diseases. For example, the genes involved in Polycystic Kidney Disease (PKD) can be expected to be expressed in BHK-cells, i.e., hamster kidney cells. Transfection of sCOGH3-clones (FIG. 4B), covering the PKD-disease gene candidate region, into BHK-cells will yield RNA-PCR products only when a promoter/5'-first segment of an exon, active in kidney cells, is cloned. Consequently, the experiment focuses directly on kidney-specific genes, thereby considerably reducing the workload of analysing all genes isolated to identify that gene which, when mutated, causes the disease.

V Detection of mutations in human genomic DNA

The current invention allows the direct detection of mutations in human genomic DNA, for example the human emerin gene[26]. This gene is located on the long arm of the X-chromosome and mutations in the gene lead to Emery-Dreifuss Muscular Dystrophy (EMD). To detect mutations in the gene, genomic DNA of a control person and a patient is amplified using a long distance PCR protocol[11] enabling the production of PCR-ed fragments of over 10 kb. To facilitate cloning in the vectors described, the forward primer, hEMa, is chosen from a site in intron 1 of the emerin gene and the reverse primer, hEMb, is chosen from a site located downstream of the 3' end of the emerin gene. After PCR, the genomic PCR product is adapted with a BmaHI-site, ligated into the BamHI-site of, e.g., sCOGH1 and the ligation mixture is used to transfect V79 cells (see Example I). The vector derived promoter will produce RNA of the vector and insert sequences and after propagation of the cells, the RNA is isolated and used for RNA-PCR analysis (as in Example I). Since a ligation mixture is used, the transfected material is a mixture of inserts in the sense and the antisense orientation. A 3'RACE reaction with the forward hGHaORF primers will produce a RNA-PCR product which includes the emerin exon 2 and all downstream exonic gene segments, including the 3'-terminal emerin exon. Several methods can now be used to compare the products derived from different sources (e.g., a control and a patient) and to determine the occurrence of sequence variation between these products (e.g., SSCP[27], heteroduplex analysis[28], PTT[10]). For example, transcription and translation of the products derived from a control person will show in which of the three products the emerin sequences are fused in frame with the hGH-exon 2 sequence as well as the size of the fused peptide produced. Similar analysis of these products from a patient (e.g., LB1520[26]) will show that the full-size peptide product observed in the control is not produced in the patient but, instead, a shorter truncated peptide appears. Consequently, it can be concluded that the patient carries a mutation, a disease causing mutation, in the coding region of the emerin gene which causes disruption of the normal reading frame and a premature translation termination.

Exon trapping in combination with PCR.

A In vitro scanning of complex genomic regions for the presence of exonic gene segments.

To scan large genomic regions for the presence of segments of exons, the region of interest (e.g., a YAC covering a disease gene candidate region) is first loaded into exon trapping molecule (e.g., the sCOGH2-vector). The loaded exon trapping molecules are transferred to either a eukaryotic cell or an in vitro transcription/RNA-processing system, to enable the isolation of a processed RNA molecule.

Third, the processed RNA molecule is isolated and analysed by, e.g., RNA-PCR. In this situation the predominant RNA will contain the 'empty' exon trapping molecule sequences only since in 50% of the clones the insert has the antisense orientation. Removal of these sequences can be achieved in several ways, e.g., by a size selection of the initial RNA-PCR products obtained. Alternatively, exon trapping molecules as sCOAP1 can be used, which prevent the production of empty products (see above). Depending on the complexity of the RNA-PCR products obtained, individual fragments are, e.g., excised from a gel and analysed directly (e.g., by translation to detect large open reading frames) or the mixture of products is cloned and individual cloned inserts are analysed.

B. Functional analysis of computer-predicted exonic gene segments.

Functional analysis of computer-predicted exonic gene segments (e.g., by GRAIL, Gene-ID, etc.) is performed by first transferring (e.g., directly by PCR or by cloning in the sCOGH2-vector) the genomic DNA segment containing the region to analyse (e.g., derived from the sequenced clone or a YAC covering the region) into an exon trapping molecule. Second, the loaded exon trapping molecule is transferred to either a eukaryotic cell or an in vitro transcription/RNA-processing system, to enable the isolation of a processed RNA molecule. Third, the processed RNA molecule is isolated and analysed by, e.g., RNA-PCR to determine its structure and its sequence and to compare this structure with the computer-predicted structure.

C. Functional analysis of potential RNA-processing mutations responsible for human genetic disease.

To analyse mutations which might affect RNA-processing, e.g., RNA splicing or transcription, the genomic DNA segment containing the potential mutation is first loaded into an exon trapping molecule (e.g., directly by PCR or by PCR and cloning in the sCOGH2-vector). Second, the loaded exon trapping molecule is transferred to either a eukaryotic cell or an in vitro transcription/RNA-processing system, to enable the isolation of a processed RNA molecule. Third, the processed RNA molecule is isolated and analysed by, e.g., RNA-PCR to determine its structure and its sequence and to compare this structure with the normal structure.

D. Detection of mutations in human genomic DNA.

To scan a human disease gene for the presence of mutations, the genomic DNA segment containing the potential disease gene is first loaded into an exon trapping molecule (e.g., directly by PCR or by PCR and cloning in the sCOGH2-vector). Second, the loaded exon trapping molecule is transferred to either a eukaryotic cell or an in vitro transcription/RNA-processing system, to enable the isolation of a processed RNA molecule. Third, the processed RNA molecule is isolated and analysed by, e.g., RNA-PCR to determine its structure, to determine the presence of translation terminating mutations (e.g., after in vitro transcription and translation), to scan for mutations in general (e.g., by SSCP, DGGE, or HD) and/or to determine its sequence and to compare this with that derived from a normal gene.

REFERENCES

1. Duyk, G. M., et al. (1990) Proc.Natl.Acad.Sci.U.S.A. 87:8995–8999.
2. Buckler, A. J., et al. (1991) Proc.Natl.Acad.Sci.U.S.A. 88:4005–4009.
3. Auch, D., et al. (1990) Nucl.Acids Res. 18: 6743–6744.
4. Hamaguchi, M., et al. (1992) Proc.Natl.Acad.Sci.U.S.A. 89: 9779–9783.
5. Datson, N. A., et al. In: Identification of Transcribed Sequences, Hochgeschwender, U., et al. New York: Plenum Press, 1994, p. 169–181.
6. Krizman, D. B., et al. (1993) Nucl.Acids Res. 21: 5198–5202.
7. Datson, N. A., et al. (1994) Nucl.Acids Res. 22: 4148–4153. (Abstract)
8. Church, D. M., et al. (1994) Nature Genet. 6: 98–105.
9. Sarkar, G., et al. (1989) Science 244: 331–334.
10. Roest, P. A. M., et al. (1993) Hum.Mol.Genet. 2: 1719–1721.
11. Cheng, S., et al. (1994) Proc.Natl.Acad.Sci.U.S.A. 91: 5695–5699.
12. Chalfie, M., et al. (1994) Science 263: 802–805.
13. YAC libraries; a users' guide, New York:W.H. Freeman and Company Publishers, 1993.
14. Maniatis, T., et al. Molecular Cloning (A laboratory manual), New York: Cold Spring Harbor Laboratory, 1989, 2nd Ed.
15. Selden, R. F., et al. (1986) Mol.Cell.Biol. 6: 3173–3179.
16. Zhuang, S., et al. (1995) Cancer Res. 55: 486–489.
17. Noteborn, M. H. M., et al. (1994) J.Virol. 68: 346–351.
18. Pierce, J. C., et al. (1992) Proc.Natl.Acad.Sci.U.S.A. 89: 2056–2060.
19. Ioannou, P. A., et al. (1994) Nature Genet. 6: 84–89.

20. Colleaux, L., et al. (1993) Hum.Mol.Genet. 2: 265–271.
21. Den Dunnen, J. T., et al. (1992) Hum.Mol.Genet. 1: 19–28.
22. Tinsley, J. M., et al. (1993) Hum.Mol.Genet. 2: 521–524.
23. Tagle, D. A., et al. (1993) Nature 361: 751–753.
24. Huxley, C., et al. (1991) Genomics 9: 742–750.
26. Bione, S., et al. (1994) Nature Genet. 8: 323–327.
27. Poduslo, S. E., et al. (1991) Am.J.Hum.Genet. 49: 106–111.
28. White, M. B., et al. (1992) Genomics 12: 301–306.
29. Troutt, A. B. et al (1992) Proc.Natl.Acad.Sci. U.S.A. 89: 9823–9825.

---

What is claimed is:

1. A method of isolating, identifying, or isolating and identifying at least one exon embedded in a segment of a eukaryotic gene, said method comprising:

cloning a DNA molecule insert comprising said exon and having a length of greater than 20 kb into a cosmid vector having two bacteriophage lambda-derived cos sites, said cosmid vector or said DNA molecule insert further comprising at least one RNA polymerase promoter, introducing said cosmid vector containing said DNA molecule insert into an environment in which transcription of DNA to RNA can occur, bringing any transcribed RNA into an environment in which processing can occur thus forming an RNA transcript, and isolating, analyzing, or isolating and analyzing said RNA transcript to isolate, analyze, or isolate and analyze said at least one exon.

2. The method according to claim 1 wherein transcription occurs in an in vitro system in the presence of an RNA polymerase.

3. The method according to claim 1 wherein processing occurs in an in vitro system.

4. The method as claimed in claim 1 wherein the RNA transcript is injected into a eukaryotic host cell allowing for processing of said RNA transcript.

5. The method of claim 1 wherein said environment in which transcription of DNA to RNA and RNA processing can occur, is a eukaryotic host cell.

6. The method of claim 5, wherein the eukaryotic host cell has a functional defect which can be complemented by a target eukaryotic gene.

7. The method of claim 5, wherein the eukaryotic host cell comprises a cell in which a target eukaryotic gene is naturally expressed.

8. The method of claim 5, wherein said eukaryotic host cell is a COS1 cell, a CHO cell, or a V79 cell.

9. The method of claim 1, wherein said DNA molecule is obtained directly from a eukaryotic cell.

10. The method of claim 1, wherein said DNA molecule is obtained by subcloning from a library of cloned eukaryotic genomic DNA.

11. The method of claim 2, wherein the RNA transcript which includes said at least one segment of the exon of the eukaryotic gene is amplified by RNA-based nucleic acid amplification.

* * * * *

UNITED STATES PATENT AND TRADEMARK OFFICE
CERTIFICATE OF CORRECTION

PATENT NO   :   5,928,867
DATED       :   July 27, 1999
INVENTOR(S) :   den Dunnen et al.

It is certified that error appears in the above-identified patent and that said Letters Patent is hereby corrected as shown below:

In column 5, line 29, after "25-40", insert --kb--;
In column 12, line 48, delete "F" and insert --T--;
In column 12, line 51 after the fourth (4$^{th}$) "T" in the sequence, insert a --T--;
In column 17, line 7, insert --25. Heikoop, J.C., et al. (1995) Eur. J. Hum. Genet. in press.--.

Signed and Sealed this

Eighteenth Day of April, 2000

*Attest:*

Q. TODD DICKINSON

*Attesting Officer*          *Director of Patents and Trademarks*